US012589179B1

(12) United States Patent
Yang et al.

(10) Patent No.: US 12,589,179 B1
(45) Date of Patent: Mar. 31, 2026

(54) CLEANING DEVICE WITH PET INTERACTION FUNCTION

(71) Applicant: Shenzhen Antop Technology Co., Ltd., Shenzhen (CN)

(72) Inventors: Ruidian Yang, Shenzhen (CN); Chu Yan, Shenzhen (CN)

(73) Assignee: Shenzhen Antop Technology Co., Ltd., Shenzhen (CN)

( * ) Notice: Subject to any disclaimer, the term of this patent is extended or adjusted under 35 U.S.C. 154(b) by 0 days.

(21) Appl. No.: 19/252,686

(22) Filed: Jun. 27, 2025

(30) Foreign Application Priority Data

Dec. 31, 2024 (CN) ........................ 202423319885.X
Apr. 27, 2025 (CN) ........................ 202520811766.1
Apr. 27, 2025 (CN) ........................ 202520811770.8

(51) Int. Cl.
| | |
|---|---|
| *B01D 46/00* | (2022.01) |
| *A01K 15/02* | (2006.01) |
| *A61L 9/16* | (2006.01) |
| *B01D 50/00* | (2022.01) |

(52) U.S. Cl.
CPC .............. *A61L 9/16* (2013.01); *A01K 15/025* (2013.01); *B01D 46/00* (2013.01); *B01D 50/00* (2013.01); *A61L 2209/10* (2013.01)

(58) Field of Classification Search
CPC ................................. B01D 46/00; B01D 50/00
See application file for complete search history.

(56) References Cited

FOREIGN PATENT DOCUMENTS

CN 221043994 U * 5/2024

* cited by examiner

*Primary Examiner* — Robert A Hopkins
(74) *Attorney, Agent, or Firm* — MUNCY, GEISSLER, OLDS & LOWE, P.C.

(57) ABSTRACT

A cleaning device with a pet interaction function includes a device body, a track formed on a side surface of the device body, and one or more movable elements that is capable of moving along the track for interacting with a pet. Considering the energetic, playful and curious nature of the pet, the cleaning device provides an interesting interactive experience that attracts the pet to approach and linger near an air purifier, increasing the chances of pet hair being adsorbed and filtered, thereby improving the cleaning effect.

20 Claims, 16 Drawing Sheets a                    b                    c d e f g h i j k

400

425

426

400

530    520    510

100

300        500

200

540

541

120

110

110

A          A

250

30                                                       300

CLEANING DEVICE WITH PET INTERACTION FUNCTION

CROSS REFERENCE TO RELATED APPLICATIONS

The present application claims priorities from Chinese Application No. CN 202423319885.X filed on Dec. 31, 2024, Chinese Application No. CN 202520811766.1 filed on Apr. 27, 2025, and Chinese Application No. CN 202520811770.8 filed on Apr. 27, 2025, all of which are hereby incorporated herein by reference.

TECHNICAL FIELD

The present disclosure relates to the field of household appliances, and in particular, to a cleaning device with a pet interaction function.

BACKGROUND

In modern society, with the improvement of people's living standards and the enhancement of living environments, pets have gradually become an indispensable member of many households. However, while bringing companionship and joy to people, the pets also bring some daily troubles, among which the most prominent being pet hair shedding. Pet hair may scatter in various corners of indoor spaces, affecting home cleanliness, and may also carry bacteria, allergens, etc., posing a potential threat to the health of dwellers. For example, a cleaning device can effectively improve the indoor air quality and plays a crucial role in solving the issue of pet hair. Through an internal filtration system, the cleaning device, such as a commonly used air purifier, can adsorb and filter out pollutants like pet hair, dust, and pollen in the air, creating a cleaner and healthier indoor environment for people. However, the current air purifier available on the market lack features for interaction with the pets except being focusing on air purification function, which limits its ability to attract pets close enough for timely pet hair collection, resulting in the accumulation of pet hair and reduced cleaning effect.

SUMMARY

Therefore, the present disclosure provides a cleaning device with a pet interaction function, including a device body, a track formed on a side surface of the device body, and one or more movable elements that are capable of moving along the track for interacting with a pet. Considering the energetic, playful and curious nature of the pet, the cleaning device provides an interesting interactive experience that encourages the pet to approach and linger near it, increasing the chances of hair being adsorbed and filtered, thereby improving the cleaning effect.

Another aspect of the present disclosure provides an improved cleaning device. A limiting portion is provided to further limit the movement of the movable elements interacting with the pet on the track. With such configuration, during nighttime or rest periods, the movement of the movable elements can be limited to prevent the pet from shifting it, thereby avoiding noise that may disrupt people's rest.

According to the cleaning device in the present disclosure, the limiting portion may be an accommodating space formed on an inner side of the track and extending into the device body, which is configured to receive or store the movable elements when pet interaction with the device is not desired.

According to the cleaning device in the present disclosure, the limiting portion may also be a positioning element arranged on the track for directly limiting the movement of the movable elements along the track.

DETAILED DESCRIPTION OF THE EMBODIMENTS

Figure 1:
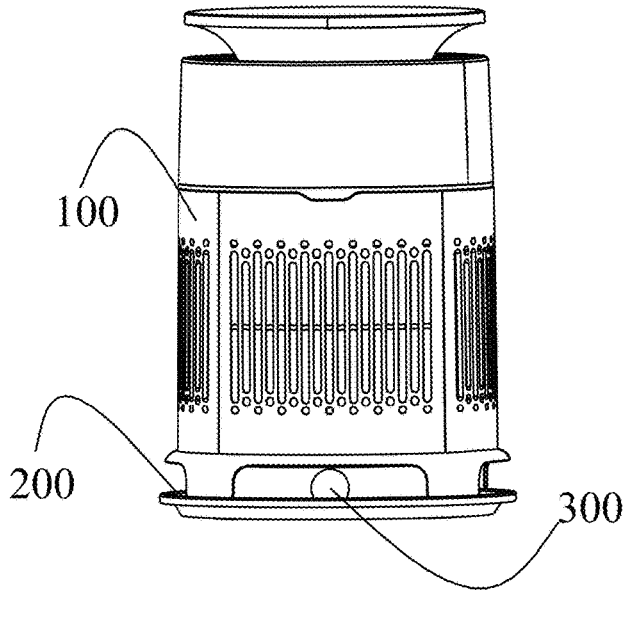
FIG. 1 is a perspective view of a cleaning device according to an embodiment of the present disclosure.

The accompanying drawings of the present disclosure are merely for exemplary descriptions, and should not be construed as a limitation on the present disclosure. To better illustrate the following embodiments, some components in the accompanying drawings may be omitted, enlarged, or reduced in size, and do not represent the actual dimensions of a product. For those skilled in the art, it is understandable that some well-known structures and descriptions thereof in the accompanying drawings may be omitted.

In the drawings, identical or similar structures are labelled with the same reference numerals.

FIG. 1 provides a cleaning device with a pet interaction function according to an embodiment of the present disclosure, particularly an air cleaner. The cleaning device includes a device body 100, a track 200 formed on a side surface of the device body 100, and one or more movable elements 300 that are capable of moving along the track 200 for interacting with a pet. The device body 100 is configured to absorb shedding hair and dander from the pet while purifying air, which eliminates the need for manual cleaning of the pet hair, as well as achieving the purpose of air cleaning. To attract the pet to approach the device body 100 and linger near it for a period of time, the track 200 is provided on the side surface of the device body 100, and the movable elements 300 are arranged in the track 200 to attract the pet to shift, bringing the pet closer to the cleaning device and encouraging the pet to linger nearby. This increases the chances of the hair being adsorbed and filtered, and thus enhances the cleaning effect.

Figure 2:
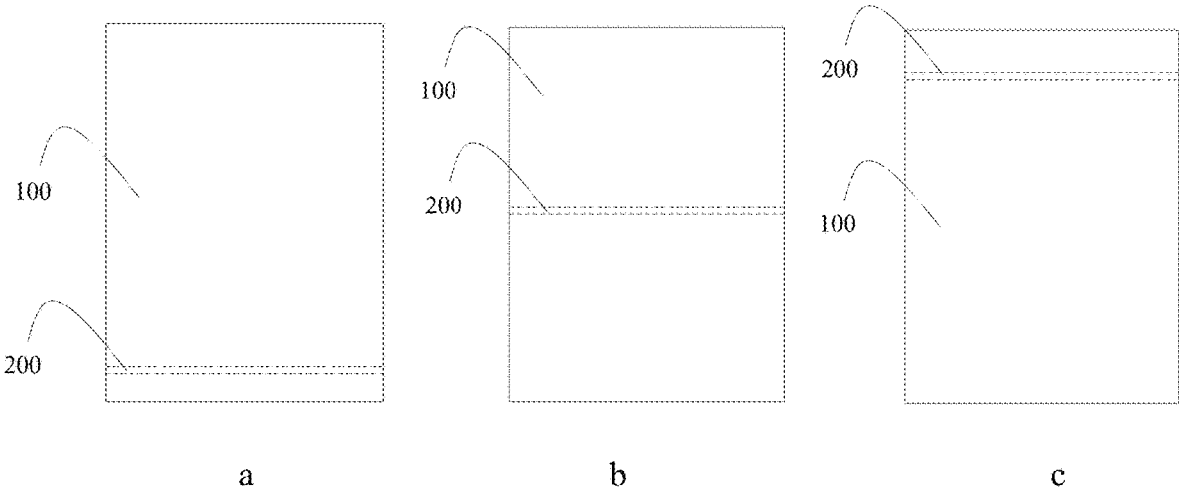
FIG. 2 is a schematic distribution diagram of a single track according to an embodiment of the present disclosure.
Figure 3:
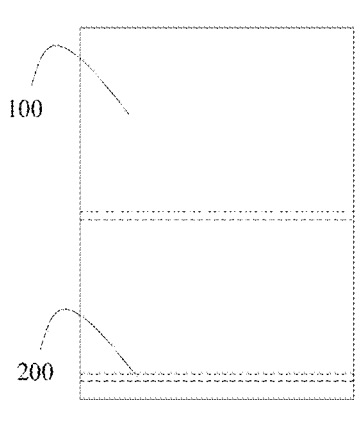
FIG. 3 is a schematic distribution diagram of a plurality of tracks according to an embodiment of the present disclosure.
Figure 3:
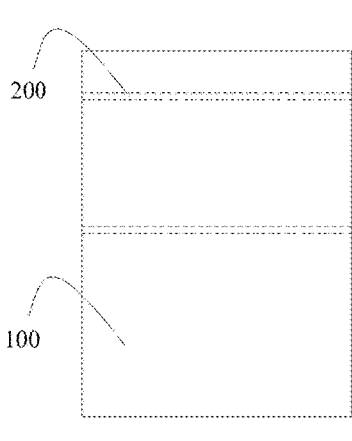
Figure 3:
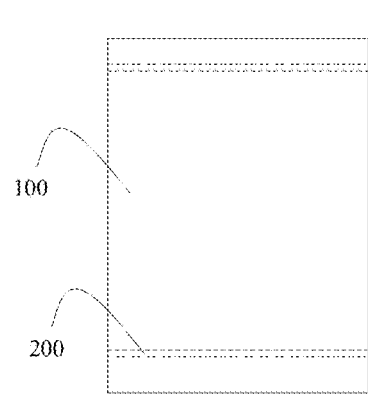
Figure 3:
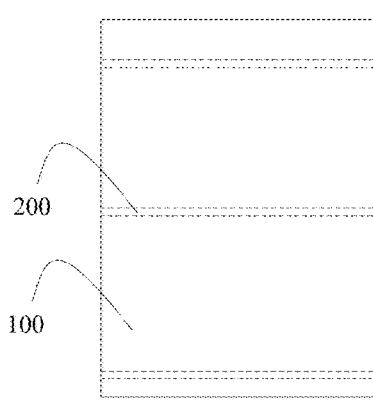
Figure 3:
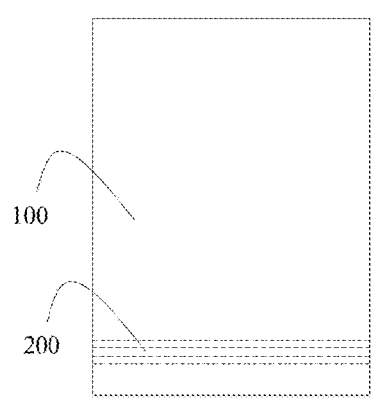
Figure 4:
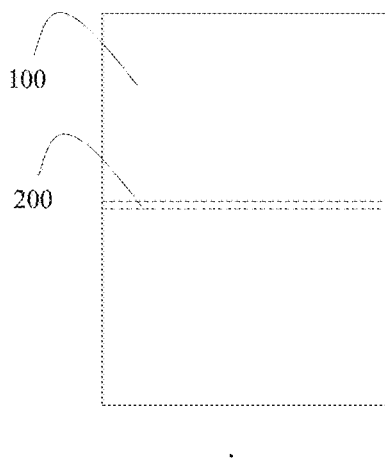
FIG. 4 is a schematic distribution diagram of tracks of different shapes according to an embodiment of the present disclosure.
Figure 4:
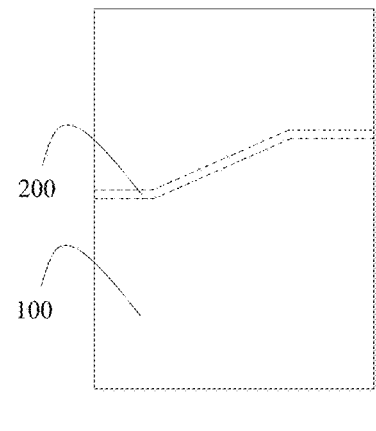
Figure 4:
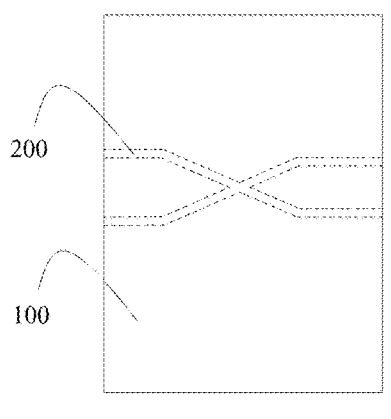

Referring to FIG. 2 to FIG. 4, the track 200 may be a circular track encircling the side surface of the device body 100, which may be arranged at a lower portion, a middle portion, or an upper portion of the device body 100, as shown in a, b, and c of FIG. 2. Alternatively, tracks 200 are arranged at both the lower portion and the middle portion of the device body 100, or both the upper portion and the middle portion, or both the upper portion and the lower portion, or the upper portion, the middle portion, and the lower portion, or a plurality of tracks 200 are simultaneously arranged at the lower portion, as shown in d, e, f, g, and h of FIG. 3. Particularly, the track 200 may include a flat circular track, a stepped circular track, a plurality of parallel circular tracks, or a plurality of staggered circular tracks, as shown in i, j, and k of FIG. 4, which can enhance the fun of pet play. Such track arrangement can increase the possibility of attracting the pet and encourage the pet to linger in front of the device body for a long time, thereby facilitating better cleaning of the pet hair or grooming the pet.

The movable elements 300 are typically spheres or Archimedean polyhedrons, which facilitates smooth sliding of the movable elements 300 on the track 200.

Figure 5:
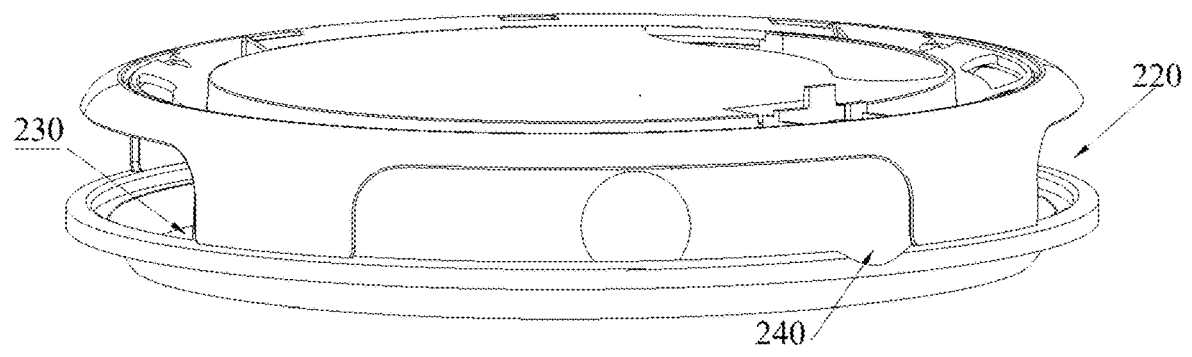
FIG. 5 is a perspective view of a track according to an embodiment of the present disclosure.
Figure 6:
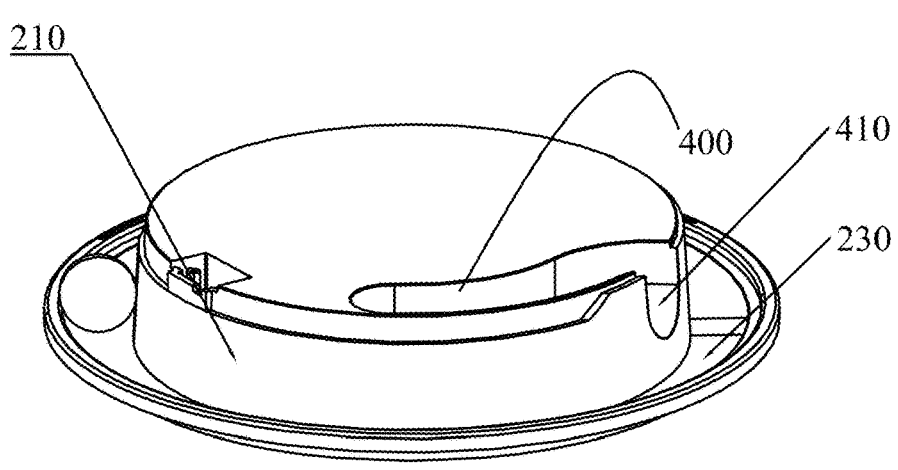
FIG. 6 is a partial perspective view of a track showing an accommodating space according to an embodiment of the present disclosure.

FIG. 5 depicts a perspective view of a track according to an embodiment of the present disclosure. The track 200 in the present embodiment is in a structure of an inwardly recessed sliding groove formed on the side surface of the device body 100. The track has a track opening 220 formed on the side surface of the device body 100. The track opening 220 allows the pet or a user to shift the movable elements, enhancing smooth movement of the movable elements. A bottom surface 230 of the track 200 may be an arc-shaped surface, as shown in FIG. 6, or a groove, preferably a groove with a size smaller than the movable elements 300, as shown in FIG. 5, which allows the movable elements 300 to roll or slide thereon. To prevent the movable elements 300 from sliding out of the track 200 when shifted by the pet, the size of the track opening 220 is smaller than the diameter of the movable elements 300.

To allow for replacement of the movable elements 300 and increase the fun of interactions with the pet, a notch 240 may be directly formed in the track 200 for taking out and putting into the movable elements 300. The notch 240 is slightly smaller than the movable elements 300 to prevent the movable elements 300 from sliding out of the track 200 when shifted by the pet. In such case, when required to be taken out, the movable element 300 is shifted to the notch 240 and pulled out of the notch 240 by applying a force from the inside to the outside; while when required to be added, the movable element 300 is directed to the notch 240 and pushed into the notch 240 by applying a force from the outside to the inside.

In order to avoid noise from the pet interacting with the movable element 300 during nighttime or other rest periods, which may disrupt the dwellers, a limiting portion may be provided to further limit the movement of the movable element that interacts with the pet on the track.

Figure 7:
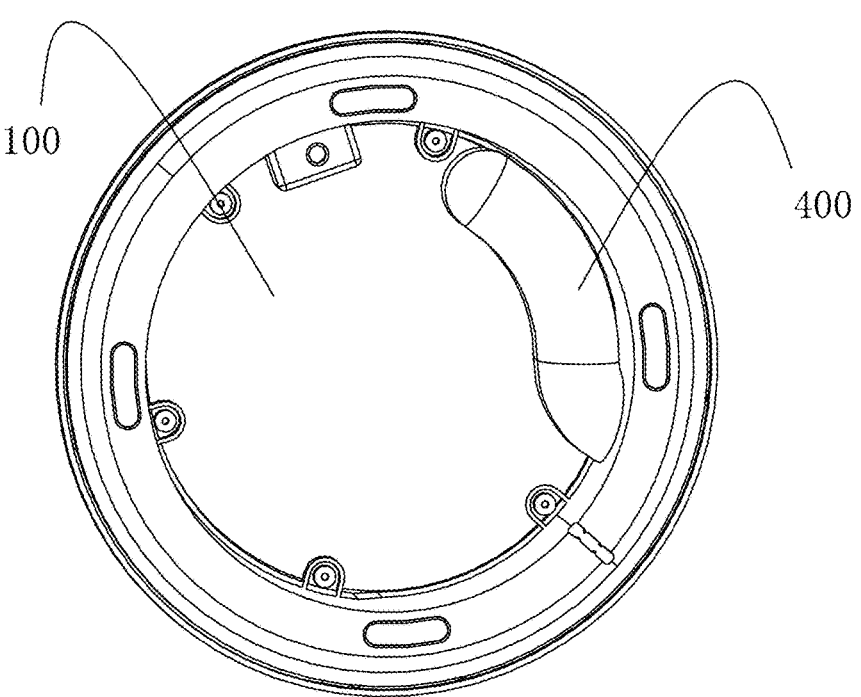
FIG. 7 is a top view of a track with a curved tubular accommodating space according to an embodiment of the present disclosure.
Figure 8:
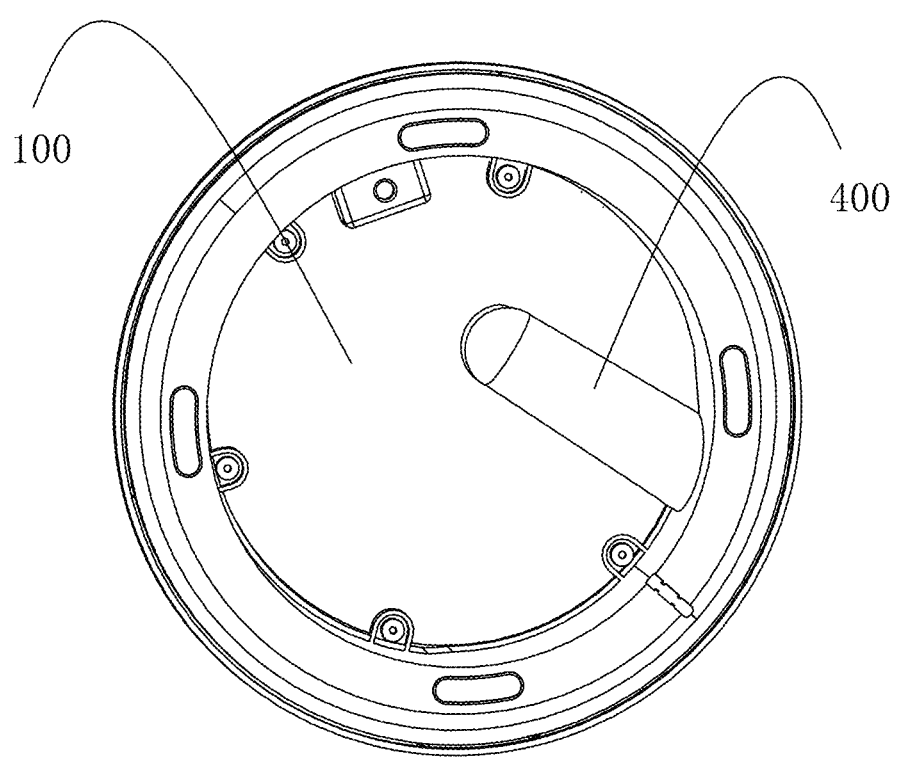
FIG. 8 is a top view of a track with a straight tubular accommodating space according to an embodiment of the present disclosure.

Referring now to FIG. 6 to FIG. 8, according to an embodiment of the present disclosure the limiting portion may be an accommodating space 400 formed on an inner side 210 of the track 200 and extending into the device body, which is configured to receive the movable elements 300 when the interaction with the pet is not desired, thereby avoiding the movement of the movable elements on the track. In this embodiment, the accommodating space 400 is of a tubular structure with a sectional size corresponding to the movable elements 300, and allows the movable elements 300 to be arranged in sequence within the accommodating space 400 for storage. This design prevents the movable elements 300 from shaking, tilting, or pressing against each other during storage, thereby improving the stability and reliability of storage. More specifically, the accommodating space 400 may be of a straight tubular structure, as shown in FIG. 8, the accommodating space 400 of the straight tubular structure facilitates storage and sliding out of the movable elements 300. Alternatively, the accommodating space 400 may be of a curved tubular structure distributed along the inner side 210 of the track 200, as shown in FIG.

7. The tubular structure distributed along the inner side 210 of the track can well utilize space at the bottom of the device.

Figure 9:
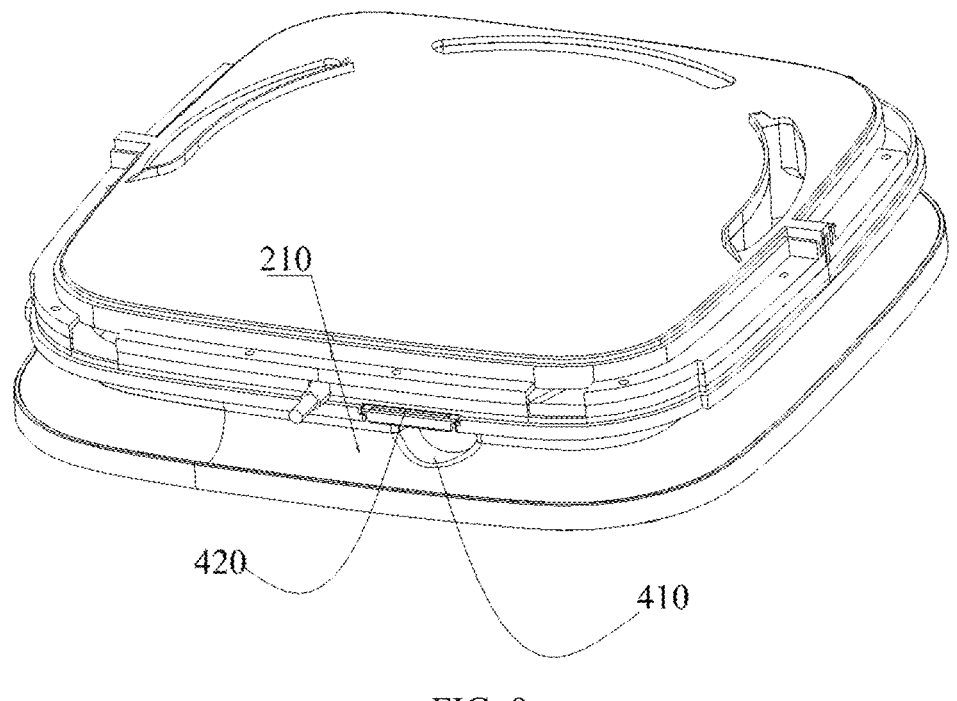
FIG. 9 is a perspective view of a track with a limiting mechanism according to an embodiment of the present disclosure.
Figure 10:
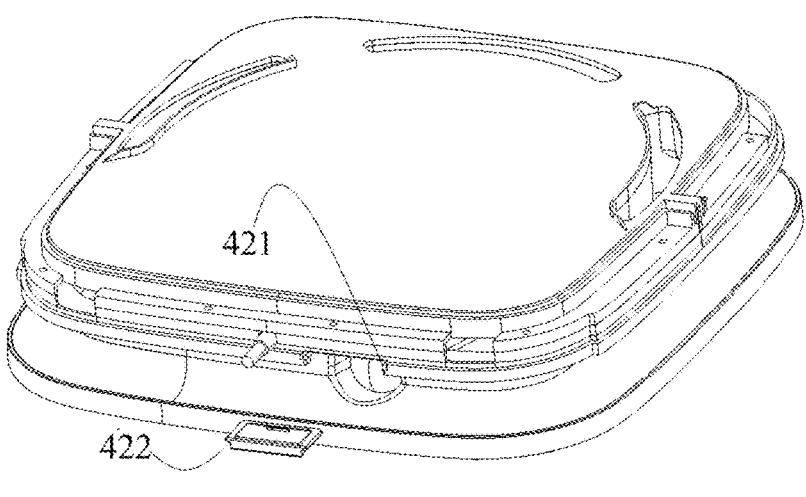
FIG. 10 is a perspective view of a track showing a specific structure of a limiting mechanism according to an embodiment of the present disclosure.
Figure 11:
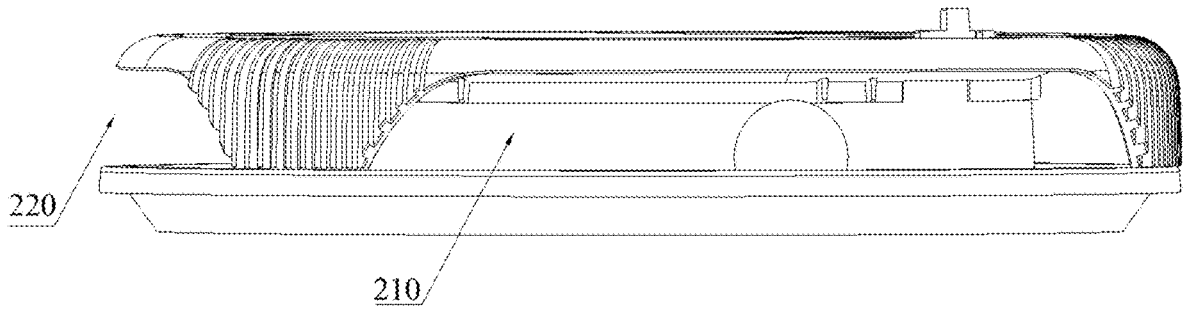
FIG. 11 is a perspective view of another track according to an embodiment of the present disclosure.
Figure 12:
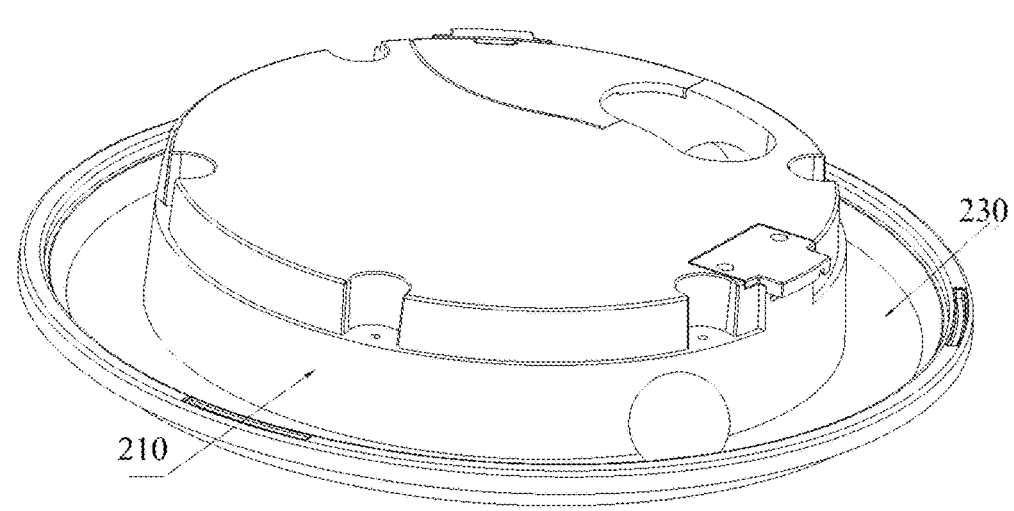
FIG. 12 is a partial schematic structural diagram of the track in FIG. 11.

Referring to FIG. 9 and FIG. 10, the accommodating space 400 forms an accommodating opening 410 in the inner side 210 of the track 200. To prevent the movable elements 300 from entering the accommodating space 400 during non-storage time periods or sliding out of the accommodating space 400 during storage time periods, a limiting mechanism 420 is provided, at the accommodating opening 410 where the accommodating space 400 abuts against the inner side 210 of the track 200, to limit the stored movable elements 300 from re-entering the track 200. The limiting mechanism 420 is configured to narrow the accommodating opening 410, so that the size of the accommodating opening 410 is smaller than that of the movable elements 300, preventing the received movable elements 300 within the track 200 from re-entering the accommodating space 400 through the accommodating opening 410, or preventing the movable elements 300 within the accommodating space 400 from sliding into the track 200 through the accommodating opening 410. In addition, to allow the movable elements 300 to slide out smoothly, the accommodating space 400 is inclined towards the track 200. In such configuration, when the movable elements 300 are released by the limiting mechanism 420, the movable elements 300 can automatically slide out of the accommodating opening 410 along a passage of the accommodating space 400 under the force of gravity and enter the track 200 for normal use, thereby completing the release of the movable elements 300.

As shown in FIG. 10, to quickly open and close the accommodating opening and facilitate storage or removal of the movable elements, the limiting mechanism 420 may include a slot 421 formed in the top surface of the track 200 and an insert 422 which is able to be inserted into the slot 421. The insert 422 limits the opening size of the accommodating opening 410 when inserted in the slot 421. After the insert 422 is taken out, the opening of the accommodating opening 410 restores and becomes larger than the track opening 220, thereby allowing the movable elements 300 to enter or be placed into the track 200 or the accommodating space 400 through the accommodating opening 410, or to be taken out of the device body 100.

Alternatively, to allow the movable elements to slide out smoothly, the limiting mechanism 420 may also be arranged at the bottom of the accommodating space 400 to limit the received movable elements 300 from entering the track 200. When the movable elements 300 are released by the limiting mechanism 420, the size of the accommodating opening 410 becomes larger than that of the movable elements 300, so that the movable elements 300 can slide out of the accommodating opening 410 along the tubular structure of the accommodating space 400 and enter the track 200, thereby completing the release of the movable elements 300.

Figure 13:
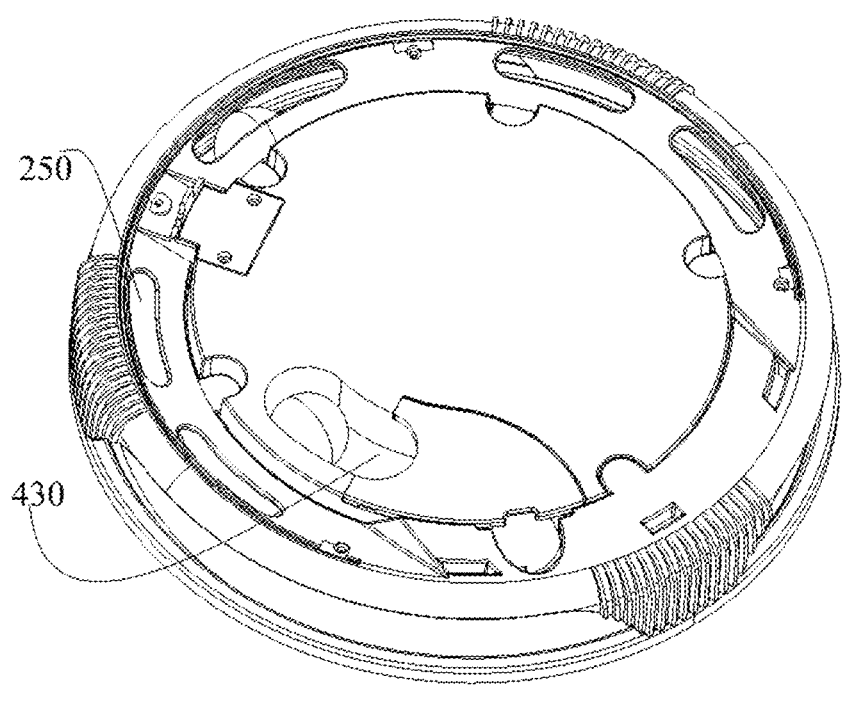
FIG. 13 is a perspective view of a track with air vents according to an embodiment of the present disclosure.
Figure 14:
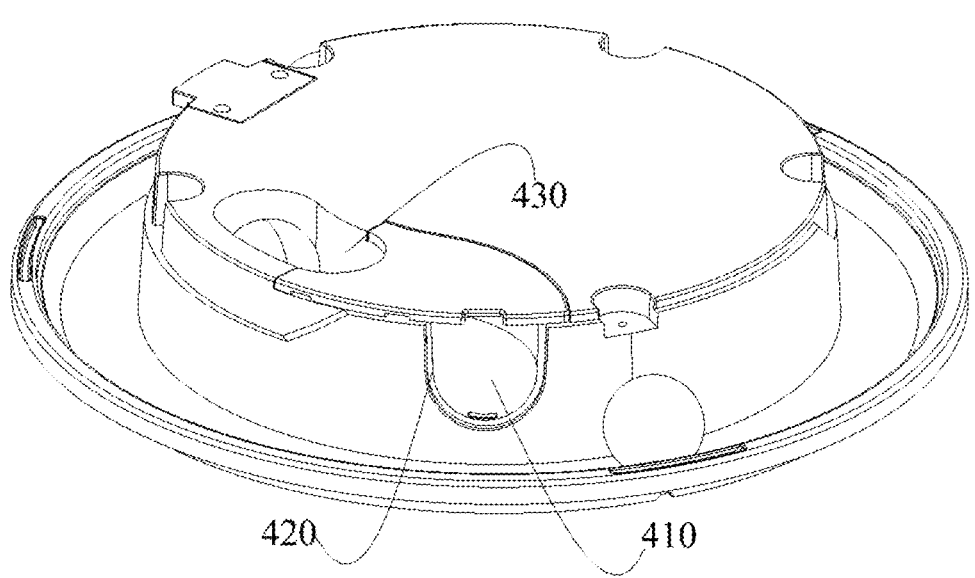
FIG. 14 is a partial schematic structural diagram of the track in FIG. 13.

FIG. 11 to FIG. 15 illustrate a track 200 according to another embodiment of the present disclosure. As shown in FIG. 13, the top surface of the track 200 in this embodiment is provided with air vents 250 which communicate with external air and lead to an interior of the device body 100, so that pet hair and dander that fall onto the movable elements 300 and the track 200 can be absorbed by the device body 100. As shown in FIG. 14, the accommodating opening 410 formed in the inner side 210 of the track 200 extends inward to form the accommodating space 400. In this embodiment, the size of the accommodating opening 410 is slightly larger than that of the movable elements 300, allowing for easy putting into and sliding out of the movable elements 300.

Figures 15, 16:
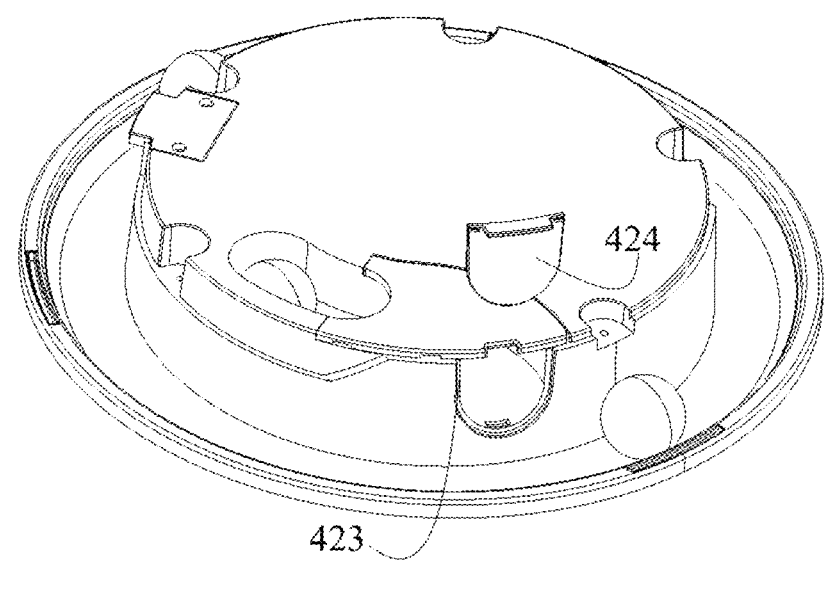
FIG. 15 is a partial schematic structural diagram of a track with another limiting mechanism according to an embodiment of the present disclosure.
FIG. 16 is a perspective view of another track with air vents according to an embodiment of the present disclosure.

In conjunction with FIG. 14 and FIG. 15, the limiting mechanism 420 in this embodiment includes an insert receptacle 423 and an insert plate 424. The size of the insert plate 424 substantially corresponds to the accommodating opening 410. When the insert plate 424 is inserted into the insert receptacle 423, the accommodating opening is in a closed state, so that the movable elements 300 in the track 200 and the movable elements 300 in the accommodating space 400 are prevented from entering or sliding out of the accommodating space 400 through the accommodating opening 410, respectively. When the insert plate 424 is removed from the insert receptacle, the accommodating opening is in an open state, so that the movable elements 300 in the track 200 and the movable elements 300 in the accommodating space 400 are allowed to enter or slide out of the accommodating space 400 through the accommodating opening 410, respectively. The air vent 250 close to the accommodating opening 410 may also be used to assist in inserting or removing the insert plate 424.

As shown in FIG. 14, one end of the accommodating space 400 in this embodiment is formed as a hidden opening 430 for replacement of the movable elements 300. The opening of the hidden opening 430 is larger than each movable element 300, which is easy to take out and put into the movable elements 300. In such configuration, when the movable element 300 needs to be taken out or placed in, an upper half portion of the device body 100 is moved away to expose the hidden opening 430. It makes possible to replace the movable elements 430 by allowing the movable elements 300 to be removed or placed through the hidden opening 430.

Referring to FIG. 16, according to an alternative embodiment of the present disclosure, the top surface of the track 200 is provided with the air vents 250, the accommodating opening 410 is located in the inner side 210 of the track 200 corresponding to one of the air vents 250, and the accommodating opening 410 extends inward to form the accommodating space 400, namely the air vent 250 also communicates with the accommodating space 400. In addition to adsorbing pet hair that falls onto the movable elements 300, the track 200, and the accommodating space 400, such air vent 250 may also be configured for directly taking out and placing the movable elements 300. For this purpose, the opening of the air vent 250 located at the accommodating opening 410 is slightly larger than the movable elements 300. When the movable element 300 needs to be taken out, a housing of the device body 100 corresponding to the air vent 250 is opened to expose the complete air vent 250, and the movable element 300 in the track 200 is taken close to the air vent 250 and pushed outward. When the movable element 300 needs to be placed, the housing of the device body 100 corresponding to the air vent 250 is opened to expose the complete air vent 250, and the movable element 300 is directed to the air vent 250 located at the accommodating opening 410 and be placed therein. In this embodiment, the replacement of the movable element 300 is completed through the air vent 250 located at the accommodating opening 410, without the additional hidden opening 430.

Figure 17:
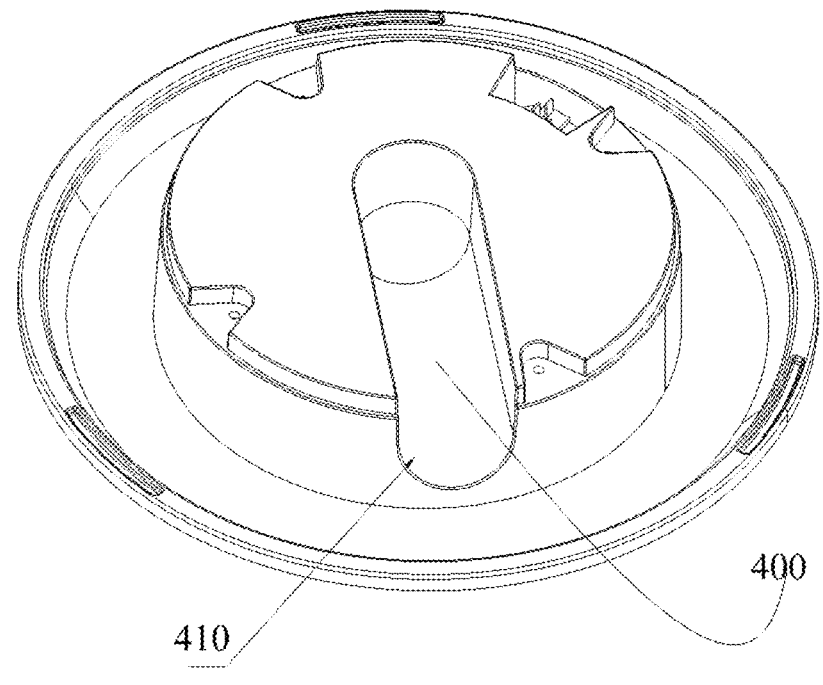
FIG. 17 is a schematic structural diagram of a track showing another accommodating space according to an embodiment of the present disclosure.
Figure 18:
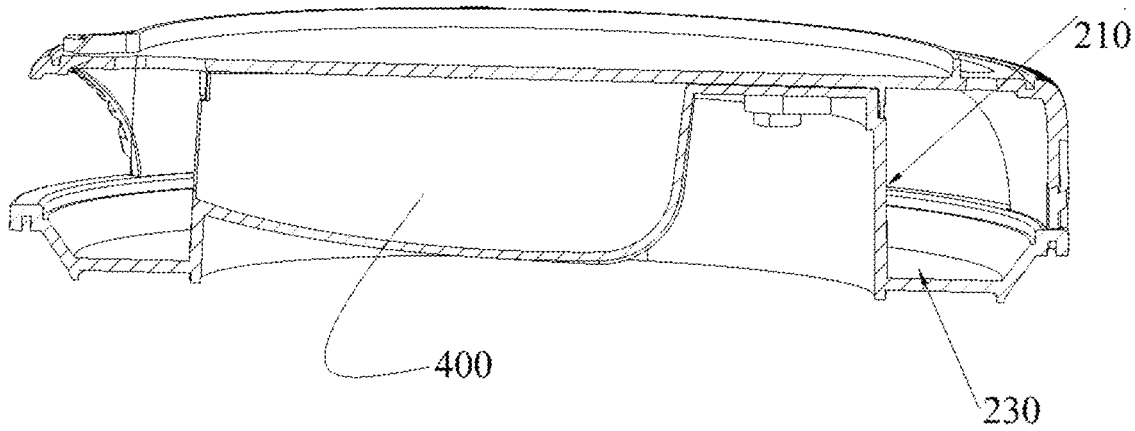
FIG. 18 is a sectional view of the track in FIG. 17 passing through the accommodating space.

Referring to FIG. 17 and FIG. 18, according to an alternative embodiment of the present disclosure, the accommodating space 400 may also be inclined away from the track 200, thereby allowing the movable elements 300 to slide to the bottom of the accommodating space 400 under the force of gravity, and then achieving the storage of the movable elements 300. When stored, the movable elements 300 are pushed into the accommodating opening 410 and then enter the accommodating space 400, and finally slide to the bottom of the accommodating space 400 along the tubular structure of the accommodating space 400. When the movable elements 300 need to be released, the device body 100 is inclined, such that the bottom of the tubular structure of the accommodating space 400 is higher than the accommodating opening 410 to allow the movable elements 300 to slide out of the accommodating opening 410 along the tubular structure and re-enter the track 200.

Figure 19:
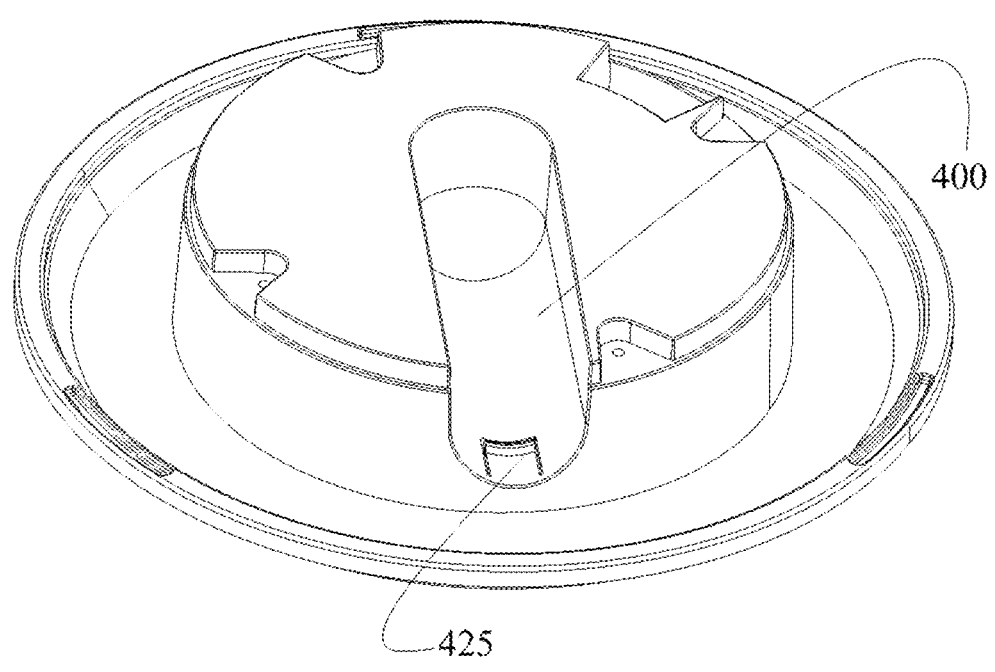
FIG. 19 is a schematic structural diagram of a track with another limiting mechanism according to an embodiment of the present disclosure.
Figure 20:
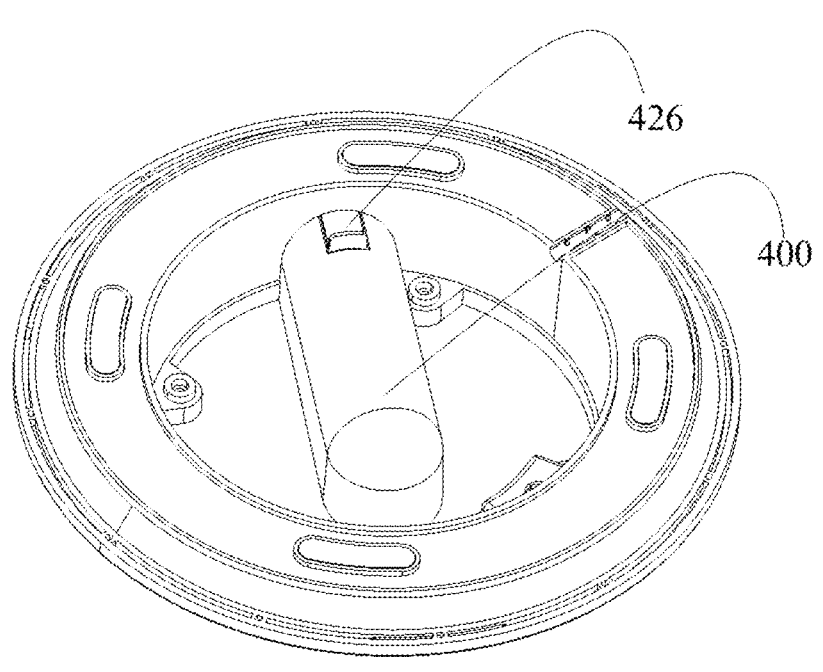
FIG. 20 is a bottom view of FIG. 19.

Referring to FIG. 19 and FIG. 20, according to an alternative embodiment of the present disclosure, the limiting mechanism 420 may include a limiting elastic sheet 425 and a limiting paddle 426. The limiting elastic sheet 425 springs up under normal conditions, Under the action of the limiting elastic sheet 425, the movable elements 300 cannot enter or exit the accommodating space 400. The limiting elastic sheet 425 serves as a barrier. When required to be stored, the movable element 300 is pushed into the accommodating opening 410. Upon contact with the limiting elastic sheet 425, the movable element 300 compresses the limiting elastic sheet 425 down under the force applied, thereby allowing the movable element 300 to enter the accommodating space 400. Once being no longer compressed, the limiting elastic sheet 425 springs up again to block the movable element 300 from sliding out of the accommodating space 400. When the movable element 300 needs to be released, the limiting paddle 426 at the bottom of the device is pressed to apply a downward force onto the limiting elastic sheet 425, causing the limiting elastic sheet 425 not to spring up, and enabling the movable element 300 to slide out of the accommodating space 400 and re-enter the track 200.

In addition to the accommodating space 400 for receiving the movable element 300 to avoid movement thereof, the limiting portion may also be a positioning element 500 arranged on the track 200 to directly limit the movement of the movable element 300 along the track 200, which prevents the pet from shifting the movable element 300 during nighttime or other rest periods to generate noise that could disturb the dwellers.

Figure 21:
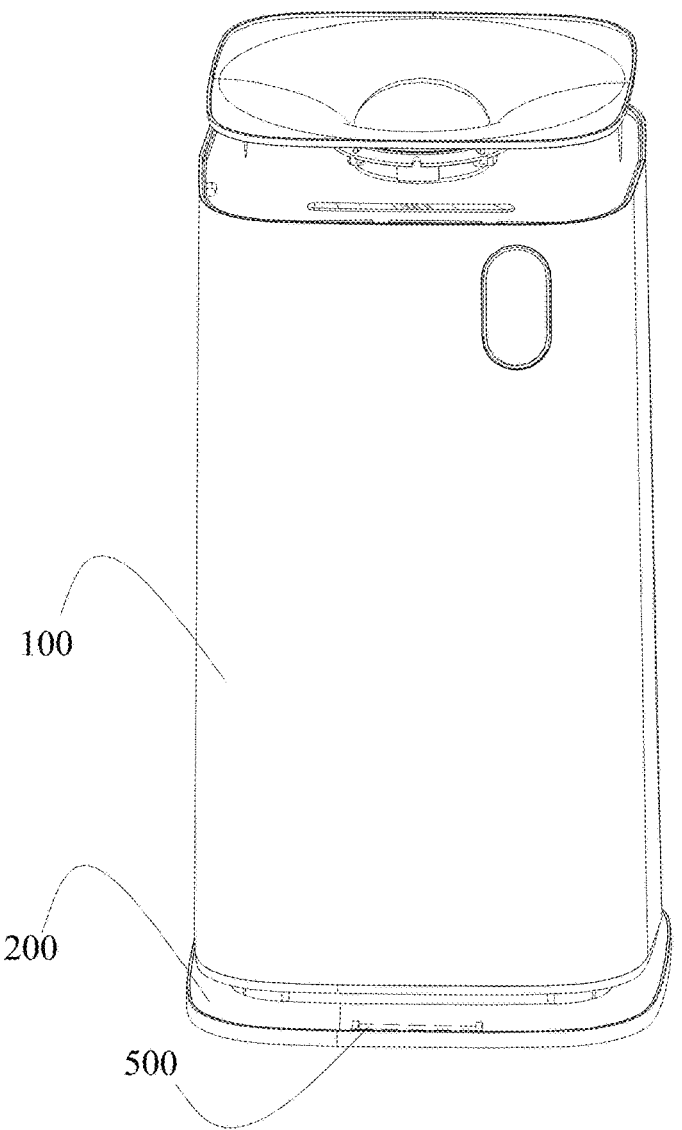
FIG. 21 is a perspective view of a cleaning device with a track having a positioning element according to an embodiment of the present disclosure.
Figure 22:
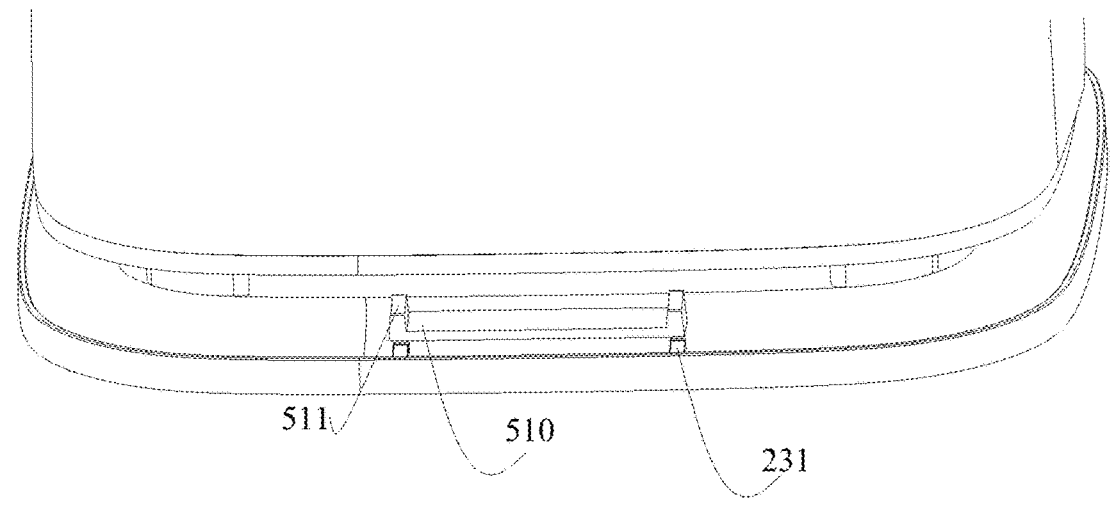
FIG. 22 is a partially enlarged view of a bottom in FIG. 21.
Figure 23:
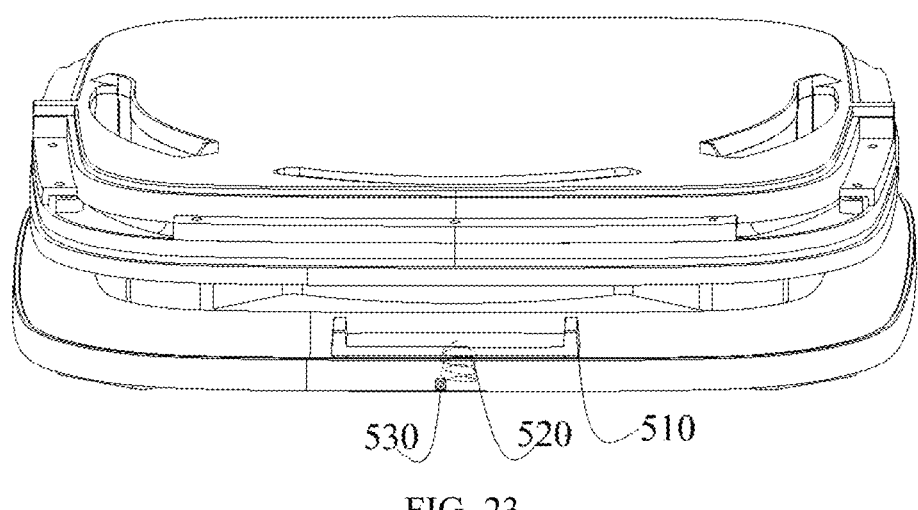
FIG. 23 is a perspective view of a track showing the positioning element according to an embodiment of the present disclosure.

In conjunction with FIG. 21 and FIG. 22, the positioning element 500 may include a floating protrusion 510 arranged on the bottom surface 230 of the track 200. The bottom surface 230 of the track 200 is provided with a through hole 231 to accommodate the floating protrusion 510. When raised, the floating protrusion 510 is located on two sides of the one or more parallel movable elements 300 to locking the movable elements 300 in place, and thus preventing the movable elements from moving. As a result, even if the pet tries to shift the movable element, no noise will be generated. When sank down, the floating protrusion 510 is located within the through hole 231, namely, below the bottom surface 230. As shown in FIG. 23, in order to control the ascending and descending of the floating protrusion 510, a synchronous connector 520 connected to the floating protrusion 510 is further provided at the bottom of the floating protrusion 510, and a triggering piece 530 is arranged at the device body 100 corresponding to the synchronous connector 520. When interaction between the pet and the movable element 300 is not desired, that is, when the movable element 300 needs to be fixed to prevent shifting by the pet, the movable element 300 is moved into the floating protrusion 510, and the triggering piece 530 is triggered to allow the synchronous connector 520 to raise the floating protrusion 510, so that the movable element is locked within the floating protrusion 510, thereby preventing noise caused by the pet shifting the movable element 300. When the movable element 300 needs to be released, the triggering piece 530 is manually triggered to allow the synchronous connector 520 to lower the floating protrusion 520, thereby releasing the movable element 300.

To engage with the bottom surface 230 of the track 200, the floating protrusion 510 is accommodated at the bottom of the track 200 under normal conditions, and the top of the floating protrusion 510 is provided with a concave arc-shaped surface 511. When the floating protrusion 510 is sank down, the arc-shaped surface 511 is flush with the bottom surface 230 of the track, allowing the movable element to pass through smoothly for normal use.

Figure 24:
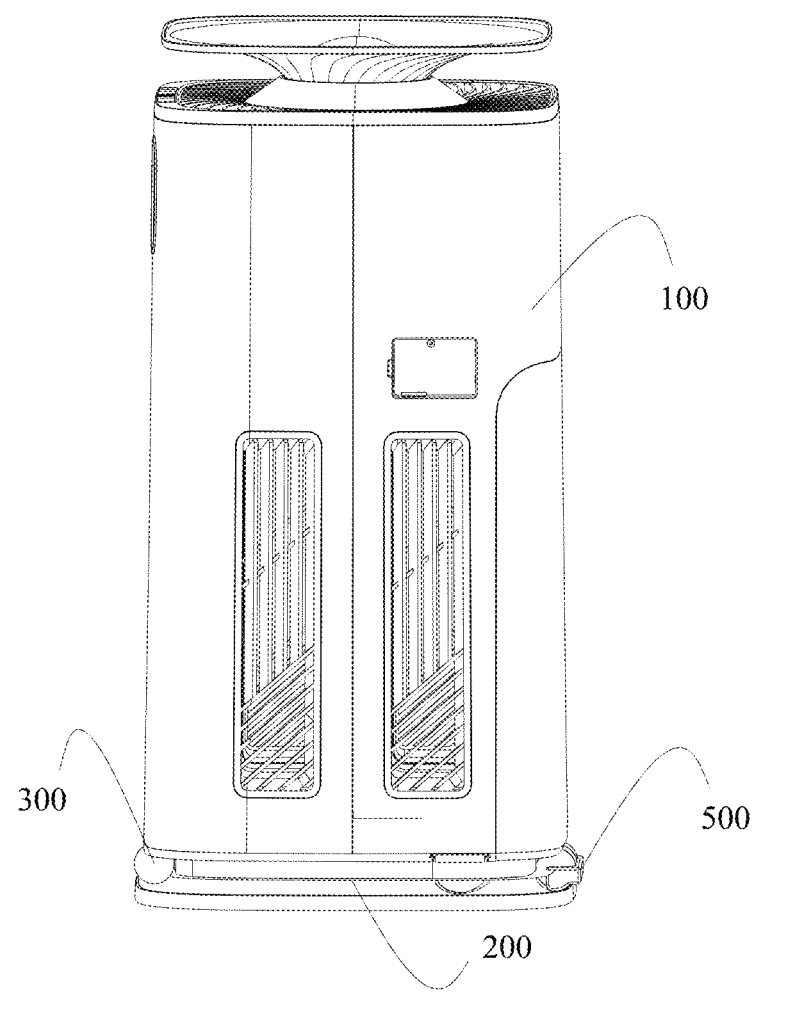
FIG. 24 is a perspective view of a cleaning device with a track having another positioning element according to an embodiment of the present disclosure.
Figure 25:
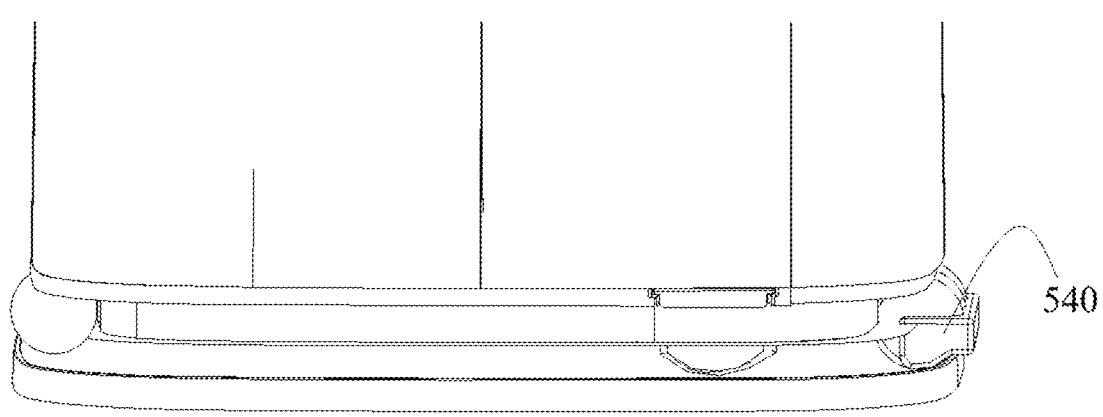
FIG. 25 is a partially enlarged view of a bottom of the cleaning device in FIG. 24.
Figure 26:
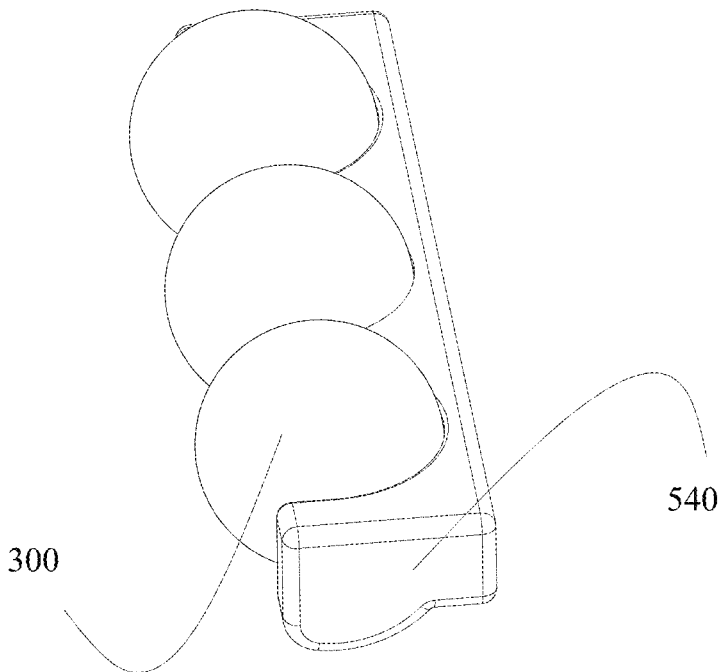
FIG. 26 is a schematic structural diagram showing a positioning element engaged with the movable elements according to an embodiment of the present disclosure.
Figure 27:
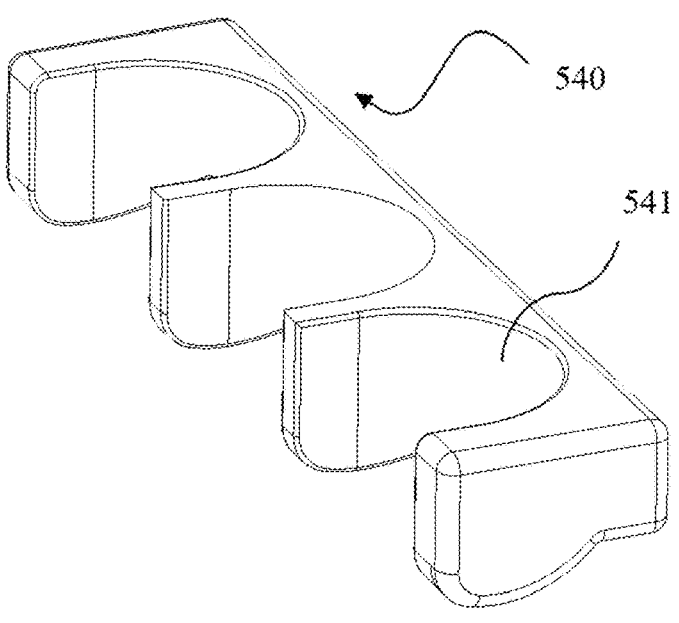
FIG. 27 is a perspective view of the positioning element in FIG. 26.

In conjunction with FIG. 24 and FIG. 25, according to an alternative embodiment, the positioning element 500 may include a clamping block 540 for clamping one or more parallel movable elements 300. The clamping block 540 is provided with a plurality of clamping portions 541, and each clamping portion 541 is configured to independently clamp one movable element 300. When interaction between the pet and the movable elements 300 is not desired, for example, during rest periods when the movement of the movable elements 300 needs to be limited to avoid noise caused by the pet shifting the movable elements 300, the movable elements 300 are shifted together, and the clamping block 540 is manually inserted into the track 200. This causes the clamping block 540 to be embedded into the track 200, with the movable elements 300 being correspondingly confined within the clamping portions 541, as shown in FIG. 26. The movable elements 300 can be released by simply removing the clamping block 540 from the track 200. As shown in FIG. 27, the bottom of the clamping block 540 that is embedded into the track 200 has a shape engaged with the bottom surface 230. After the movable elements 300 are released, the clamping block 540 may be accommodated at the bottom of the track 200 to ensure smooth sliding of the movable elements 300 on the track 200. The clamping block 540 may be made of hard or soft rubber with a certain degree of compressibility, and the clamping block 540 tightly fits into the track 200 or is slightly larger than the track 200, allowing the positioning element 500 to remain securely in place within the track 200 without shifting easily.

Figure 28:
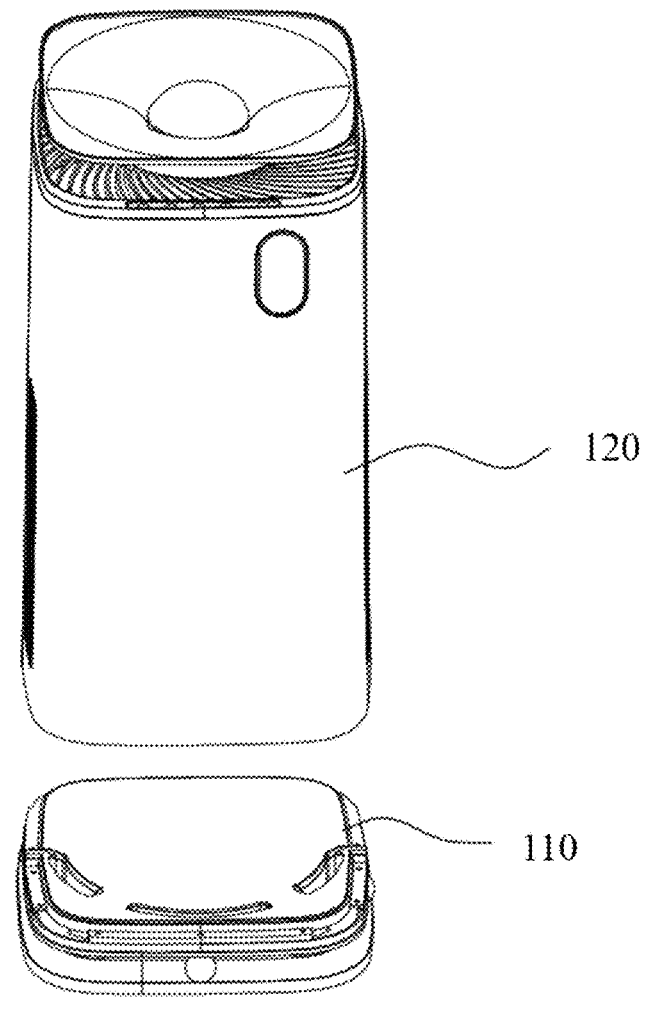
FIG. 28 is an exploded view of a cleaning device according to an embodiment of the present disclosure.

FIG. 28 illustrates an exploded structural diagram of a cleaning device according to an embodiment of the present disclosure. The device body 100 of the cleaning device in this embodiment particularly includes a base 110 and a main body 120 arranged on the base 110.

Figure 29:
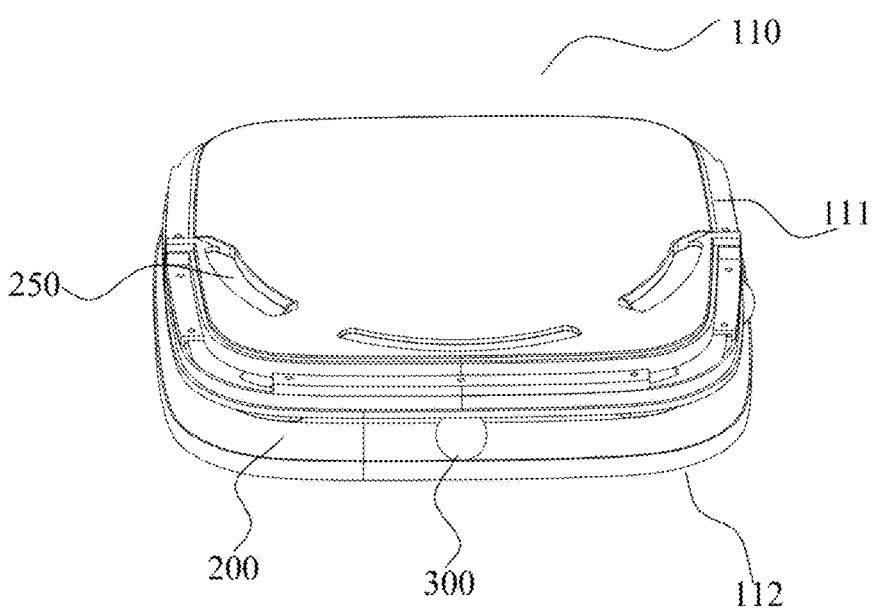
FIG. 29 is a view showing a base of the cleaning device according to an embodiment of the present disclosure.
Figure 30:
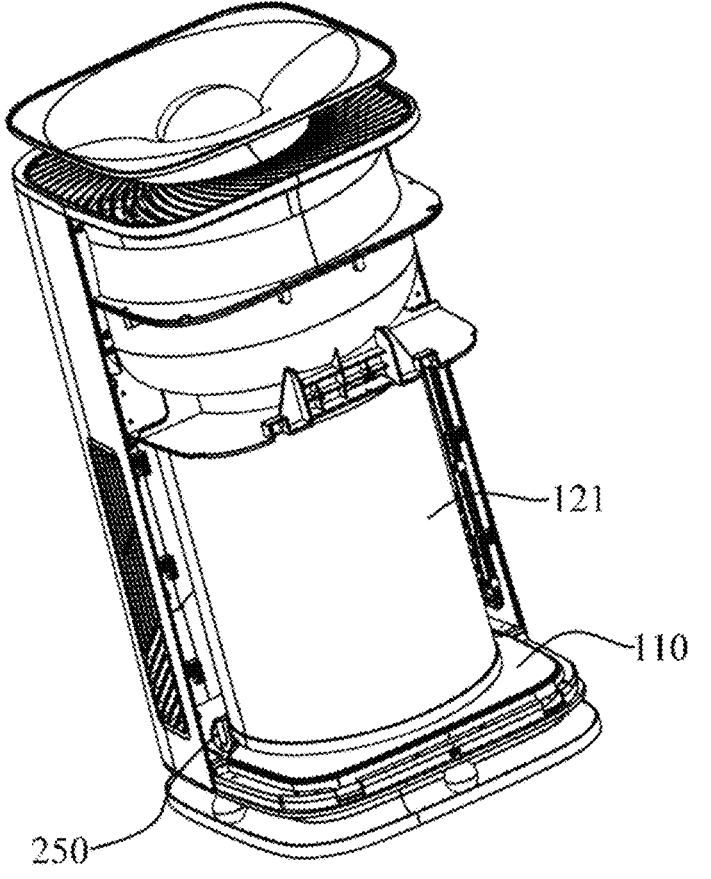
FIG. 30 is perspective view showing an internal structure of the cleaning device in FIG. 28, with some portions omitted.

Referring to FIG. 29, according to an embodiment of the present disclosure, the base 110 of the device body 100 particularly includes an upper-layer base 111 and a lower-layer base 112 arranged below the upper-layer base 111. The track 200 is defined between the upper-layer base 111 and the lower-layer base 112. The upper-layer base 111 is provided with air vents 250, and the track 200 is provided with a plurality of movable elements 300 that can move along the track 200 for interacting with the pet. As shown in FIG. 30, the main body 120 includes a filter screen 121. One end of each air vent 250 communicates with the external air, and the other end communicates with the filter screen 121 of the main body 120.

The base 110 in this embodiment can optimize the purification capability of the cleaning device, which can collect and purify pet hair or hair balls that fall onto the ground, while also having an interactive function for the pet to enhance pet enjoyment. Specifically, the base 110 in this embodiment is cooperated with the main body 120 in a way that the main body 120 is arranged above the base 110 and the upper-layer base 111 is assembled at the bottom of a front housing and a rear housing of the main body 120, the front housing, the rear housing, and the base 110 being enclosed to form a filter screen accommodation space. The filter screen 121 is located within the filter screen accommodation space. When the cleaning device is activated, not only can side surfaces of the main body 120 adsorb floating hair in the air, but also the pet hair or hair agglomeration near the ground can be collected into the filter screen accommodation space through the air vents 250 in the upper-layer base 111 due to the fact that the base 110 is close to the ground. The pet hair or hair agglomeration are finally adsorbed onto the filter screen 121, thereby optimizing the collection and purification capabilities for the pet hair and hair agglomeration that fall onto the ground. In addition, in this embodiment, the track 200 is formed in the base 110 and is provided with the plurality of movable elements 300 that can move along the track 200 for interacting with the pet. Therefore, the pet can shift the movable elements 300, causing the movable elements 300 to move back and forth within the track 300, thereby enhancing the pet's fun, improving interactive performance between an air purifier and the pet, and thus achieving a multifunctional effect. Furthermore, the movable elements 300 attract the pet to approach the air purifier and linger nearby, increasing the chances of the hair being adsorbed and filtered, thereby improving the cleaning effect.

Figure 31:
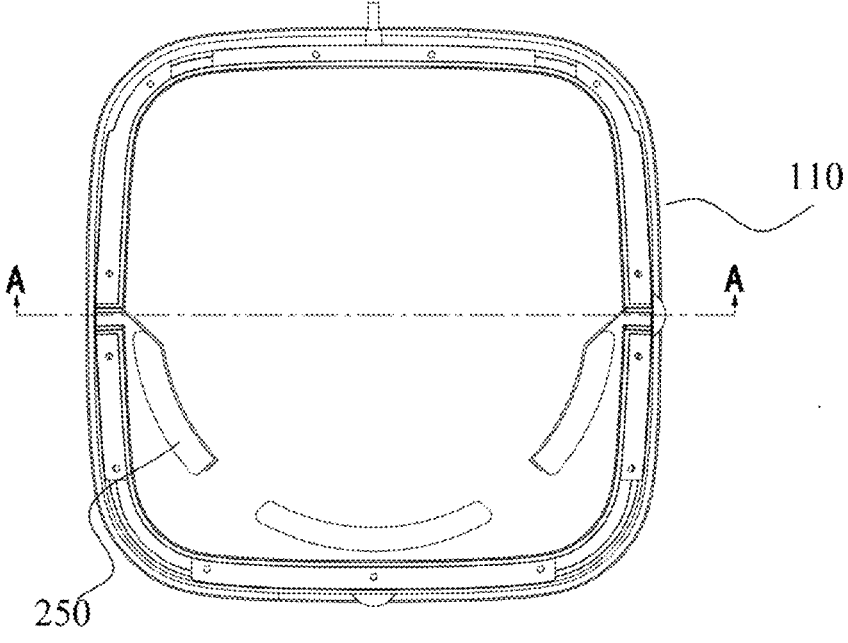
FIG. 31 is a top view of the base in FIG. 29.
Figure 32:
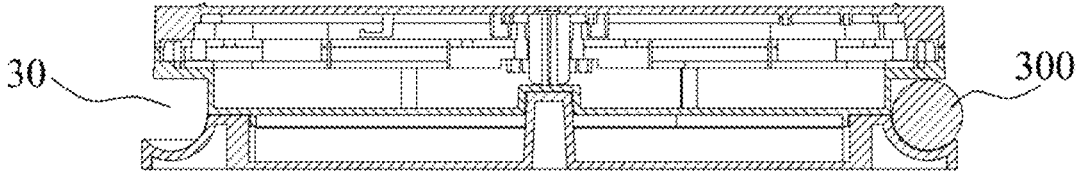
FIG. 32 is a sectional view in an A-A direction in FIG. 31.

In conjunction with FIG. 31 and FIG. 32, in this embodiment, the track 200 is of a semi-open sliding groove structure 30 that is formed in the side surface of the base 110 and recessed inward. The air vents 250 communicate with the semi-open sliding groove structure 30.

The movable elements 300 are preferably rolling or sliding elements. When the pet shifts the movable elements 300, the movable elements 300 may roll or slide within the track 200, attracting the pet to interact with them. More preferably, the movable elements 300 are of spherical structures, such as catnip balls or Archimedean polyhedrons.

Figure 33:
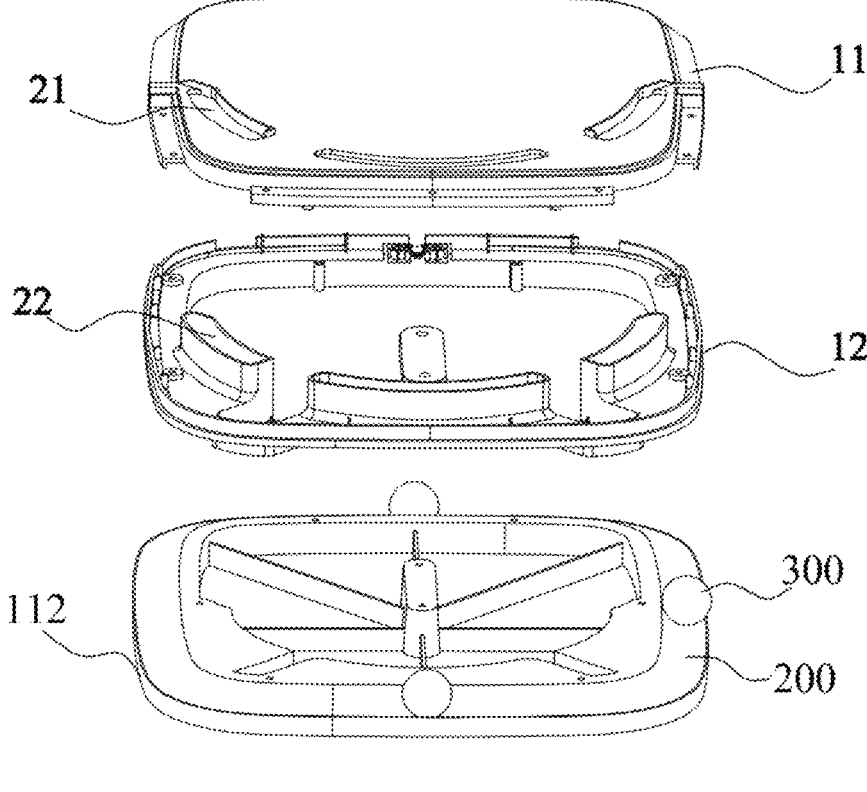
FIG. 33 is an exploded view of a base of the cleaning device according to an embodiment of the present disclosure.

Referring to FIG. 33, according to an embodiment of the present disclosure, the upper-layer base 111 may include a first base 11 and a second base 12 arranged below the first base 11 and forming a hollow space with a bottom of the first base 11. The hollow space may serve as an accommodation space for electronic components. Therefore, the base 110 in this embodiment can accommodate some electronic devices, contributing to the integration of the cleaning device.

Each air vent 250 may include a first air vent 21 formed in the first base 11 and a second air vent 22 formed in the second base 12 corresponding to the first air vent 21. The second air vent 22 communicates with the external air through the semi-open sliding groove structure 30, and the first air vent 21 communicates with the filter screen 121 in the main body 120. In such configuration, the external air and the pet hair or hair agglomeration near the ground can be adsorbed to the filter screen 121 through the second air vent 22 and the first air vent 21 in sequence.

At least two first air vents 21 are arranged, thereby increasing channels for the hair agglomeration or hair to enter and thus improving the purification efficiency. The second air vents 22 are arranged corresponding to the first air vents 21.

In this embodiment, three first air vents 21 are provided in spaced relationship along a circumferential direction of the track 200. Each first air vent 21 is in an arc shape. Correspondingly, three second air vents 22 are also in an arc shape to cooperate with the first air vents 21.

According to a preferred embodiment, to prevent the movable elements 300 from blocking part of the air vents

250 when moving near the air vents 250 and thus affecting the air purification efficiency, projections of the air vents 250 on the lower-layer base 112 are staggered from the track 200. In such way, it ensures that the movable elements 300 on the track 200 are always staggered from the air vents 250 and do not affect the air purification.

According to a preferred embodiment, to attract the pet to interact with the movable elements 300, the movable elements 300 may be designed in bright colors. Moreover, when two or more movable elements 300 are arranged, each movable element 300 may be assigned a different color.

Obviously, the above embodiments of the present disclosure are merely examples provided to clearly describe the technical solutions of the present disclosure, rather than limiting specific implementations of the present disclosure. Any modifications, equivalent substitutions, improvements, etc. made within the spirit and the principle of the claims of the present disclosure shall fall within the scope of protection of the claims of the present disclosure.

What is claimed is:

1. A cleaning device with a pet interaction function, comprising:
   a device body;
   a track formed on a side surface of the device body; and
   one or more movable elements that are capable of moving along the track for interacting with a pet,
   wherein the track is a circular track encircling the side surface of the device body, and the track is arranged at a lower portion, a middle portion, or an upper portion of the device body, or a plurality of the tracks are simultaneously arranged at the lower portion, the middle portion, or the upper portion of the device body.

2. The cleaning device according to claim 1, wherein the track is of an inwardly recessed sliding groove structure formed on the side surface of the device body, a bottom surface of the track is an arc-shaped surface or a groove, allowing the one or more movable elements to roll or slide thereon, and the track has a track opening with a size smaller than a diameter of the one or more movable elements, preventing the one or more movable elements from falling out through the track opening.

3. The cleaning device according to claim 1, wherein the track includes a flat circular track, a stepped circular track, a plurality of parallel circular tracks, or a plurality of staggered circular tracks.

4. The cleaning device according to claim 1, wherein a top surface of the track is provided with air vents communicating with the device body.

5. The cleaning device according to claim 1, wherein the one or more movable elements are of spherical structures or Archimedean polyhedrons.

6. The cleaning device according to claim 1, wherein the device body comprises a base and a main body arranged on the base, the base comprises an upper-layer base provided with air vents and a lower-layer base arranged below the upper-layer base, one end of air vents communicates with external air, the other end thereof communicates with the main body, and the track is defined between the upper-layer base and the lower-layer base.

7. The cleaning device according to claim 1, wherein an accommodating space extending into the device body is formed on an inner side of the track and is used for receiving the one or more movable elements.

8. The cleaning device according to claim 7, wherein the accommodating space forms an accommodating opening in the inner side of the track, and close to the accommodating opening, a limiting mechanism is provided to prevent the received one or more movable elements from re-entering the track.

9. The cleaning device according to claim 8, wherein the limiting mechanism comprises a slot formed in a top surface of the track or an insert receptacle nearby the accommodating opening, and an insert which is capable of being inserted into the slot or an insert plate which is capable of being inserted into the insert receptacle, and the insert or the insert plate is configured to limit an opening size of the accommodating opening.

10. The cleaning device according to claim 8, wherein the limiting mechanism comprises a limiting elastic sheet arranged within the accommodating space and close to the accommodating opening, and a limiting paddle at a bottom of the accommodating space, the limiting elastic sheet is configured to block the one or more movable elements from sliding out of the accommodating space, and the limiting paddle is configured to release blocking of the limiting elastic sheet on the movable element.

11. The cleaning device according to claim 7, wherein the accommodating space is of a tubular structure, with a sectional size corresponding to the one or more movable elements, allowing the one or more movable elements to be arranged in sequence within the accommodating space for storage.

12. The cleaning device according to claim 11, wherein the accommodating space is of a straight tubular structure or a tubular structure distributed along an inner side of the track.

13. The cleaning device according to claim 1, wherein a positioning element is arranged on the track to limit a movement of the one or more movable elements along the track.

14. The cleaning device according to claim 13, wherein the positioning element comprises a floating protrusion arranged on a bottom surface of the track, when raised, the floating protrusion is located on two sides of the one or more movable elements in parallel, and when sank down, the floating protrusion is located below the bottom surface.

15. The cleaning device according to claim 14, wherein a synchronous connector and a triggering piece are arranged below the bottom surface, the synchronous connector is connected with the floating protrusion, a through hole is formed in the bottom surface to accommodate the floating protrusion, and the triggering piece is arranged below the synchronous connector to control ascending or descending of the synchronous connector.

16. The cleaning device according to claim 14, wherein a concave arc-shaped surface is arranged at a top of the floating protrusion.

17. The cleaning device according to claim 13, wherein the positioning element comprises a clamping block for clamping the one or more movable elements in parallel by embedding into the track.

18. The cleaning device according to claim 17, wherein the clamping block is a single piece and provided with a plurality of clamping portions, and each clamping portion is configured to independently clamp one movable element.

19. The cleaning device according to claim 17, wherein a bottom of the clamping block that is embedded into the track has a shape corresponding to the bottom surface.

20. A cleaning device with a pet interaction function, comprising:
    a device body;
    a track formed on a side surface of the device body; and
    one or more movable elements that are capable of moving along the track for interacting with a pet,
    wherein a top surface of the track is provided with air vents communicating with the device body.

* * * * *